(12) United States Patent
Smith

(10) Patent No.: US 7,511,802 B2
(45) Date of Patent: Mar. 31, 2009

(54) MEASURING TRACE COMPONENTS OF COMPLEX GASES USING GAS CHROMATOGRAPHY/ABSORPTION SPECTROMETRY

(75) Inventor: Stevie Horton Smith, Seabrook, TX (US)

(73) Assignee: SpectraSensors, Inc., Rancho Cucamonga, CA (US)

(\*) Notice: Subject to any disclaimer, the term of this patent is extended or adjusted under 35 U.S.C. 154(b) by 148 days.

(21) Appl. No.: 11/726,001

(22) Filed: Mar. 19, 2007

(65) Prior Publication Data

US 2007/0273882 A1    Nov. 29, 2007

Related U.S. Application Data

(60) Provisional application No. 60/808,797, filed on May 26, 2006.

(51) Int. Cl.
*G01J 3/26* (2006.01)
*G01N 21/00* (2006.01)

(52) U.S. Cl. .................. 356/72; 356/326; 356/437

(58) Field of Classification Search .................. 356/72, 356/326, 437
See application file for complete search history.

(56) References Cited

U.S. PATENT DOCUMENTS

| | | | |
|---|---|---|---|
| 3,735,565 A * | 5/1973 | Gilby et al. | ............... 356/319 |
| 4,829,183 A | 5/1989 | McClatchie et al. | |
| 4,953,390 A | 9/1990 | Krempl | |
| 5,026,991 A | 6/1991 | Goldstein | |
| 5,107,118 A | 4/1992 | Murray et al. | |
| 5,528,040 A | 6/1996 | Lehmann | |
| 5,572,031 A | 11/1996 | Cooper et al. | |
| 5,760,895 A | 6/1998 | Kebabian | |
| 5,777,329 A | 7/1998 | Westphal et al. | |
| 5,847,392 A | 12/1998 | Van Den Berg et al. | |
| 5,880,850 A | 3/1999 | McAndrew | |
| 5,958,340 A | 9/1999 | Meyer et al. | |
| 5,963,336 A | 10/1999 | McAndrew | |
| 6,064,488 A | 5/2000 | Brand et al. | |
| 6,188,475 B1 | 2/2001 | Inman et al. | |
| 6,292,756 B1 | 9/2001 | Lievois et al. | |
| 6,353,225 B1 | 3/2002 | Strzoda et al. | |
| 6,420,695 B1 | 7/2002 | Grasdepot et al. | |

(Continued)

FOREIGN PATENT DOCUMENTS

DE    3413914 A1    10/1985

(Continued)

OTHER PUBLICATIONS

Allen, Mark G., "Diode laser absorption sensors for gas-dynamic and combustion flows", Meas. Sci. Technol.; 9:545-562 (1998).

(Continued)

*Primary Examiner*—F. L Evans
(74) *Attorney, Agent, or Firm*—Mintz, Levin, Cohn, Ferris, Glovsky and Popeo P.C.

(57) ABSTRACT

Low concentrations of complex gas mixture components may be detected and quantified using a gas-chromatograph to separate a gas mixture prior to analysis of one or more eluting components using an absorption spectrometer. Substantial reductions in analytical system complexity and improvements in reliability are achieved compared with other commonly used methods for analyzing such complex mixtures.

24 Claims, 12 Drawing Sheets

U.S. PATENT DOCUMENTS

| | | | |
|---|---|---|---|
| 6,657,198 | B1 | 12/2003 | May |
| 6,762,836 | B2 | 7/2004 | Benicewicz et al. |
| 6,841,781 | B2 | 1/2005 | Toomey |
| 7,116,422 | B2 | 10/2006 | Larking et al. |
| 7,132,661 | B2 | 11/2006 | May |
| 7,193,718 | B2 | 3/2007 | Lundqvist et al. |
| 7,228,017 | B2 | 6/2007 | Xia et al. |
| 2002/0190840 | A1 | 12/2002 | Fujita et al. |
| 2003/0213912 | A1 | 11/2003 | Tulip |
| 2006/0163483 | A1 | 7/2006 | Chabanis et al. |
| 2006/0176486 | A1 | 8/2006 | Ho |
| 2006/0192967 | A1 | 8/2006 | Kluczynski |

FOREIGN PATENT DOCUMENTS

| | | |
|---|---|---|
| EP | 0922908 | 6/1999 |
| GB | 2416205 | 1/2006 |
| WO | WO03/100393 | 12/2003 |
| WO | WO2005/047872 | 5/2005 |

OTHER PUBLICATIONS

Arroyo, et al., "Absorption Measurements of Water-Vapor Concentration, Temperature, and Line-Shape Parameters Using a Tunable INGAASP Diode Laser", Applied Optics, 32(30): 6104-6116 (Oct. 20, 1993).

Liu, Xiang, "Line-of-Sight Absorption of $H_2O$ Vapor: Gas Temperature Sensing in Uniform and Nonunimorm Flows"; Submitted to the Department of Mechanical Engineering and the Committee on Graduate Studies, in Partial Fulfillment of the Requirements for the Degree of Doctor of Philosophy, Stanford University, Jun. 2006.

May, Randy D. et al., "The MVACS tunable diode laser spectrometers", Journal of Geophysical Research, 106(E8): 17673-17682 (Aug. 25, 2001).

May, Randy D., "Correlation-based technique for automated tunable diode laser scan stabilization", Rev. Sci. Instrum.; 63(5): 2922-2926 (1992).

Silver, Joel A. Et al., "Diode laser measurements of concentration and temperature in microgravity combustion", Meas. Sci. Technol, 10:845-852 (1999).

Varga, A. et al., "Photoacoustic system for on-line process monitoring of hydrogen sulfide ($H_2S$) concentration in natural gas streams", Applied Physics B, 85: 315-321 (2006).

Webster, Christopher R. et al., "Simultaneous in Situ Measurements and Diurnal Variations of NO, $NO_2$, $O_3$, $jNO_2$, $CH_4$, $H_2O$, and $CO_2$ in the 40- to 26-km Region Using an Open Path Tunable Diode Laser Spectrometer", Journal of Geophysical Research, 92(D10): 11931-11950 (Oct. 20, 1987).

Bomse, Davis S. et al., "Frequency modulation and wavelength modulation spectroscopes: comparison of experimental methods using a lead-salt diode laser", Applied Optics; 31(6): 718-731 (1992).

Brown, L.R. et al., "Experimental Line Parameters of the Oxygen A Band at 760 nm", Journal of Molecular Spectroscopy, 199: 166-179 (2000).

Cassidy, Daniel T. et al., "Atmospheric pressure monitoring of trace gases turnable diode lasers", Applied Optics, 21(7): 1185-1190 (1982).

Cassidy, Daniel T. et al., "Trace gas detection with short-external-cavity InGaAsP diode laser transmitter modules operating at 1.58 µm", Applied Optics, 27(13): 2688-2693 (1988).

Herriott, Donald R. et al., "Folded Optical Delay Lines", Applied Optics, 4(8): 883-889 (1965).

Herriott, Donald R. et al., "Off-Axis Paths in Spherical Mirror Interferometers", Applied Optics, 3(4): 523-526 (1964).

"In-Situ Sensors for the Chemical Industry—Final Report", project report of "Development of In Situ Analysis for the Chemical Industry", the Dow Chemical Company, Principle investigator: Dr. J.D. Tate, profect No. DE-FC36-o21D14428, pp. 1-37, Jun. 30, 2006.

Kessler, William J. et al.,"Near-IR diode laser-based sensor for pb-level water vapor in industrial gases", Proceedings of the SPIE, 3537: 139-149 (1999).

May, Randy D. et al., "Data Processing and Calibration for Tunable Diode Laser Harmonic Absorption Spectrometers", Journal of Quantitative Spectroscopy and Radiative Transfer, 49(4): 335-347 (1993).

May, Randy D. et al., "Open-Path, Near-Infrared Tunable Diode Laser Spectrometer for Atmospheric Measurements of $H_2$ O", Journal of Geophysical Research, 103:19161-19172 (1998).

May, Randy D., "Computer Processing of Tunable Diode Laser Spectra", Applied Spectroscopy, 43(5): 834-839 (1989).

May, Randy D., "Next-Generation Diode Laser Gas Sensors for Environmental and Industrial Monitoring", Proceedings of the SPIE, 3858: 110-118 (1999).

Paige, Mark E., "Commercial Gas Sensing with Vertical Cavity Lasers", Advanced Semiconductor Lasers and Their Applications Conference Technical Digest; pp. 141-143 (1999).

Philippe, Louis C. et al., "Laser diode wavelength-modulation spectroscopy for simultaneous measurement of temperature, pressure, and velocity in shock-heated oxygen flows", Applied Optics, 32(30): 6090-6103 (1993).

Reid, J. et al., "Second-Harmonic Detection with Tunable Diode Lasers—Comparison of Experiment and Theory", Applied Physics, B 26: 203-210 (1981).

Richter, Dirk et al., "Development of an automated diode-laser-based multicomponent gas sensor", Applied Optics, 39(24): 4444-4450 (2000).

Rothman et al., "The HITRAN molecular spectroscopic database: edition of 2000 including updates through 2001", Journal of Quantitative Spectroscopy & Radiative Transfer, 82: 5-44 (2003).

Scott, David C. "Airborne Laser Infrared Absorption Spectrometer (ALIAS-II) for in situ atmospheric measurements of $N_2O$, $CH_4$, CO, HCL and $NO_2$ from balloon or remotely piloted aircraft platforms", Applied Optics, 38(21): 4609-4622 (1999).

Silver, Joel A., "Frequency-modulation spectroscopy for trace species detection: theory and comparison among experimental methods", Applied Optics, 31(6): 707-717 (1992).

Wang, Jian et al., "In situ combustion measurements of CO with diode-laser absorption near 2.3 µm", Applied Optics,39(30): 5579-5589 (2000).

Webster, Christopher R. et al., Aircraft (ER-2_ laser infrared absorption spectrometer (ALIAS) for in-situ stratospheric measurements of HCL $N_2$0, $CH_4$, $NO_2$, and $HNO_3$, Applied Optics, 33(3): 454-472 (1994).

Webster, Christopher R. et al., "Quantum-cascade laser measurements of stratospheric methane and nitrous oxide", Applied Optics, 40(3): 321-326 (2001).

Webster, Christopher R. et al., "Tunable diode laster IR spectrometer for in situ measurements of the gas phase composition and particle size distribution of Titan's atmosphere", Applied Optics, 29(7): 907-917 (1990).

Zhou, Xin et al., "Development of a sensor for temperature and water concentration in combustion gases using a single tunable diode laser", Measurement Science and Technology, 14: 1459-1468 (2003).

'The HITRAN Database', [online]. Harvard-Smithsonian Center for Astrophysics, 2006, [retrieved on May 8, 2007]. Retrieved from the Internet: <URL:www.cf.harvard.edu/hitran/welcometop.html>.

* cited by examiner

MEASURING TRACE COMPONENTS OF COMPLEX GASES USING GAS CHROMATOGRAPHY/ABSORPTION SPECTROMETRY

RELATED APPLICATIONS

This application claims the priority of U.S. Provisional Application for Patent Ser. No. 60/808,797, filed May 26, 2006, the disclosure of which is incorporated here in its entirety.

TECHNICAL FIELD

The subject matter described herein relates to measuring trace components of complex gas backgrounds.

BACKGROUND

Concentrations of low levels of trace species in gas mixtures, such as, for example, natural gas (methane) may be measured by a variety of different techniques, one of which is absorption spectroscopy. A light beam of suitable wavelength is passed through a cell containing the gas mixture to be analyzed. As light passes through the gas, it is partially absorbed by trace gas molecules. The amount of light absorbed depends on the concentration (partial pressure) of molecules of a species that absorbs light at the incident wavelength. Light intensity transmitted through the cell is proportional to the concentration of absorbing gas in the cell and can therefore be used as a measure of the concentration. This technique is suitable when the background gas has no absorption features in the spectral region being used for the trace gas measurement, but is less useful for complex gas mixtures because multiple compounds in the mixture may have absorption features that overlap with those of the species of interest. In the petrochemical industry, these "interfering" gases tend to be numerous and to have complex absorption spectra, as shown in Table 1, which lists representative concentrations of various species typically found in petrochemical plant vent gases.

TABLE 1

Constituent gases typically found in petrochemical plant vents.

| Component Gas | Percentage |
|---|---|
| hydrogen sulfide ($H_2S$) | 0.0085 |
| nitrogen ($N_2$) | 0.0500 |
| C1 hydrocarbons | 2.0667 |
| carbon dioxide ($CO_2$) | 97.7430 |
| C2 hydrocarbons | 0.0721 |
| C3 hydrocarbons | 0.0258 |
| IC4 | 0.0054 |
| NC4 | 0.0075 |
| IC5 | 0.0023 |
| NC5 | 0.0018 |
| neohexane | 0.0001 |
| cyclopentane | 0.0002 |
| 2-methylpentane | 0.0006 |
| 3-methylpentane | 0.0003 |
| n-hexane | 0.0010 |
| methylcyclopentane | 0.0002 |
| benzene | 0.0019 |
| cyclohexane | 0.0009 |
| 2-methylhexane | 0.0005 |
| 3-methylhexane | 0.0003 |
| trimethylcyclopentane | i |
| toluene | 0.0040 |
| 2-methylheptane | 0.0006 |
| 3-methylheptane | 0.0001 |

TABLE 1-continued

Constituent gases typically found in petrochemical plant vents.

| Component Gas | Percentage |
|---|---|
| dimethylcyclohexanes | 0.0009 |
| n-octane | 0.0004 |
| ethyl benzene | 0.0004 |
| m- & p-xylenes | 0.0011 |
| o-xylenes | 0.0006 |
| C9 naphthenes | — |
| C9 parafins | 0.0008 |
| n-nonane | 0.0001 |
| n-decane | — |
| undecane plus | 0.0002 |
| Total: | 100.0000 |

SUMMARY

In a first aspect, a first sample of a gas mixture containing a component is injected into a first gas chromatography column through which a carrier gas flows. The component is transported by the carrier gas through the first gas chromatography column and elutes from the first gas chromatography column at a known elution time. The carrier gas and the component eluting from the first gas chromatography column are supplied into a sample cell of an absorption spectrometer at the elution time. A light beam is passed through the sample cell, and an absorption of the light beam in the sample cell is measured. The absorption is converted to a concentration of the component in the sample cell.

In optional variations, A method as in claim 1, concentration of the component in the sample cell may be converted to a concentration of the component in the gas mixture. The first gas chromatography column may be operated within a temperature-controlled enclosure. A programmed temperature ramp program may be executed to vary the temperature within the temperature-controlled enclosure after injecting the first sample. A second sample of the gas mixture may be simultaneously injected into a second gas chromatography column through which the carrier gas flows. In this variation, the component is transported by the carrier gas through the second column and elutes from the second column at the known elution time and the carrier gas and the component from the second column are supplied into the sample cell of the absorption spectrometer at the elution time with the carrier gas and the component from the first column.

In additional optional variations, the light beam may be generated from a tunable diode laser. The light beam may be generated from a laser source selected from a vertical cavity surface emitting laser, a horizontal cavity surface emitting laser, a quantum cascade laser, a distributed feedback laser, and a color center laser. The light beam may be generated by a modulated laser source and the absorption spectrum may be a harmonic absorption spectrum. The light beam may be generated by a modulated laser source and the absorption spectrum may be a direct absorption spectrum. The absorption spectrometer may be a differential absorption spectrometer. A temperature within the temperature-controlled enclosure may be monitored, and the first sample may be automatically injected when the temperature is at a predetermined starting temperature.

In another interrelated aspect, an apparatus includes a first gas chromatography column, a first injector to deliver a first sample of a gas mixture into the first gas chromatography column, and an absorption spectrometer. The absorption spectrometer includes a sample cell, a laser source that generates a beam of light passing through the sample cell, and a photodetector that quantifies absorption of the light beam in the sample cell. The apparatus also includes a gas chromatograph outlet valve to divert gases exiting the gas chromatography column to the sample cell, and a process controller that controls the injector port to deliver the first sample to the first gas chromatography column at a first time and the gas chromatograph outlet valve to divert the outflow from the first gas chromatography column to the sample cell at a second time that is selected to coincide with a retention time of a component of the first gas mixture.

In further optional variations, the process controller may receive output data from the photodetector, record an absorption spectrum, and calculate a concentration of the component in the gas mixture. The absorption spectrometer may also include a microprocessor that receives output data from the photodetector, records an absorption spectrum, and calculates a concentration of the component in the gas mixture. The apparatus may also include a temperature-controlled enclosure that includes an oven heater and within which the chromatography column may be positioned. In this variation, the process controller may command the oven heater to vary the temperature within the temperature-controlled enclosure as a function of time after the first time according to a predetermined program. The apparatus may also include a temperature sensor that communicates with the process controller and that is positioned within the temperature-controlled enclosure. The process controller may monitor an output signal from the temperature sensor and use the output signal to determine when the temperature-controlled enclosure is at an appropriate temperature to begin an analysis run. The apparatus may also include a scrubber that reduces the concentration of the component and one or more scrubber valves that may be operated to direct the gases exiting the first gas chromatography column through the scrubber prior to the sample cell or to bypass the scrubber. The apparatus may also include one or more second gas chromatography columns and one or more second injectors to deliver one or more second samples of a gas mixture into the one or more second gas chromatography columns at the first time.

In a third interrelated aspect, an apparatus includes a first gas chromatography column, a first injector to deliver a first sample of a gas mixture into the first gas chromatography column, a gas chromatograph outlet valve to divert gases exiting the gas chromatography column to a sample cell of an absorption spectrometer, and a process controller. The process controller controls the injector port to deliver the first sample to the first gas chromatography column at a first time and the gas chromatograph outlet valve to divert the outflow from the first gas chromatography column at a second time that is selected to coincide with a retention time of a component of the first gas mixture.

DESCRIPTION OF THE DRAWINGS

This disclosure may be better understood upon reading the detailed description and by reference to the attached drawings, in which.

DETAILED DESCRIPTION

Figure 1:
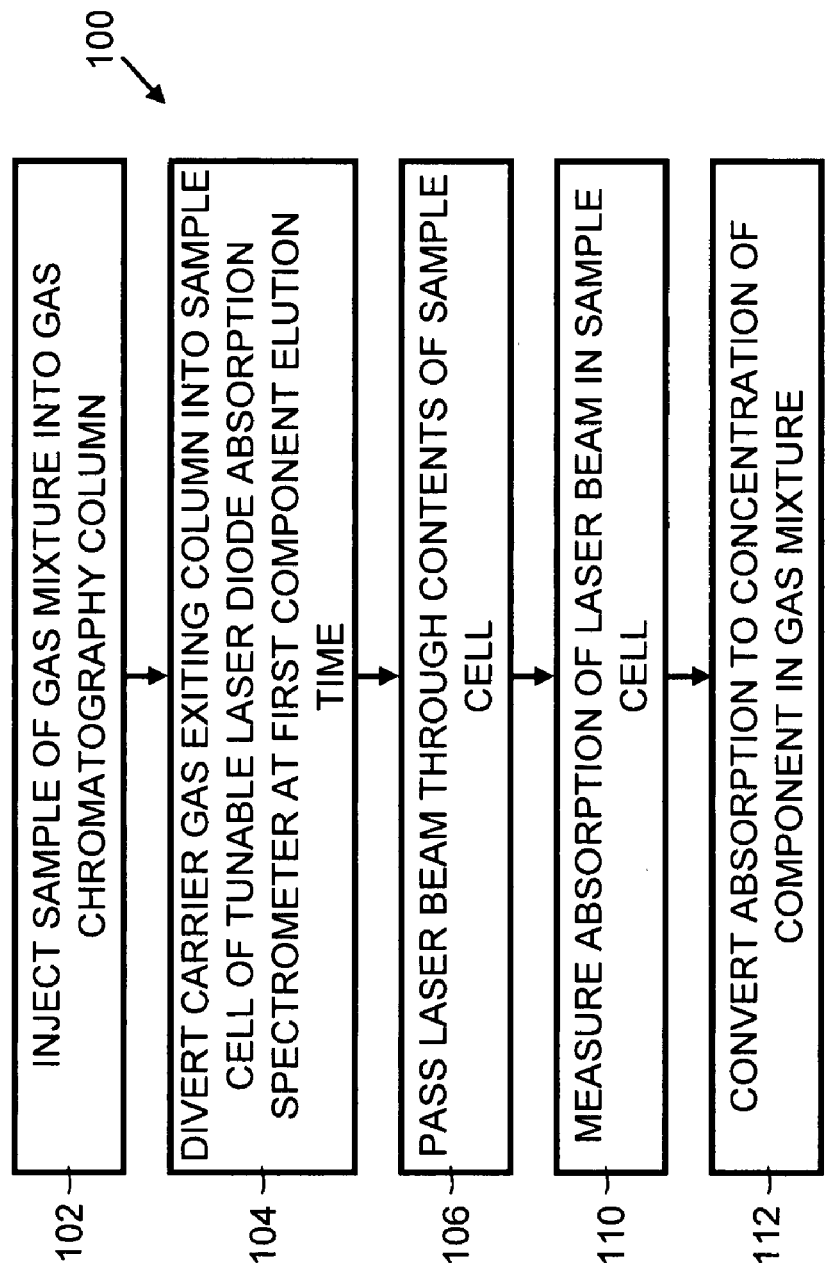
FIG. 1 is a flow chart illustrating one implementation of a method for analyzing trace components of a gas mixture.

It has been found that accurate analyses of trace components in complex gas mixtures may be attained by separating and concentrating one or more components of a gas mixture, such as, for example, with a gas chromatograph (GC) and analyzing the separated component or components with an absorption spectrometer, such as, for example, a tunable diode laser absorption spectrometer. A GC separates components of a gas mixture that contains multiple chemical species. This separation is reproducible for a given column operated under the same temperature and carrier gas flow conditions.

A gas mixture may include a mixture of many components in a complex matrix. For mixtures containing unknown compounds, the components may be at least partially separated to facilitate identification of individual components by various detection schemes. Gas chromatography may be used to separate volatile organic compounds as well as higher molecular weight compounds. In general, a gas chromatograph (GC) includes a separation column containing a stationary phase, a mobile phase (generally, a carrier gas) flowing through the stationary phase, an injector for delivering a sample to the column, one or more detectors, and a data recording system. Components of the gas mixture may be separated as they pass through the column due to differences in their partitioning behavior between the mobile carrier gas and the stationary phase. Different compounds have different retention times in the column due to differences in molecular size, volatility, and tendency to adsorb on the stationary phase material in the column. Sample components that partition strongly into the stationary phase spend a greater amount of time in the column and are separated from components that stay predominantly in the mobile phase and pass through the column faster.

Carrier gases may be inert gases such as helium, argon, nitrogen, or the like. Other carrier gases may be suitable depending on the chemical makeup of the gas mixture. The injector may be a controlled orifice or other means for injecting the sample. The injector may be maintained at a temperature higher than the boiling point of the least volatile component in the sample mixture to facilitate quantitative transfer of the sample to the column. Because partitioning behavior between the mobile and stationary phases is typically temperature-dependent, a GC column may be operated within a thermostat-controlled oven or other temperature-controlled enclosure. Gas mixture components with a wide range of boiling points may be separated by ramping the oven temperature from a low starting temperature to a higher ending temperature. Temperature ramp profiles may be modified depending on the content of the sample being tested. A GC may include one or more detectors to analyze the separated components of an injected sample as they elute from the column. Typical detectors include atomic-emission detectors (AED), chemi-luminescence detectors, electron-capture detectors (ECD), flame-ionization detectors (FID), flame-photometric detectors (FPD), mass spectrometers (MS), nitrogen-phosphorus detectors (NPD), photo ionization detectors (PID), and thermal conductivity detectors (TCD). The subject matter disclosed herein adds valuable capabilities, such as very high sensitivity, reliability and accuracy are available with relatively little or no maintenance over long periods of time.

Low levels of trace gases in gas mixtures may be measured using absorption spectroscopy. A light beam of suitable wavelength may be passed through a sample cell containing the gas to be measured. As light passes through the gas contained in the sample cell, some of the light intensity is absorbed by gas molecules. The amount of light absorbed is dependent on the concentration (partial pressure) of absorbing components present in the sample cell and may therefore used as a measure of the concentration of a component in the sample cell which can be used to calculate the concentration of that component in the original gas mixture.

In one implementation, a method as shown in the flow chart 100 of FIG. 1 may be used. A sample of the gas mixture is injected into a gas chromatography (GC) column 102. The GC column may be in a GC oven or other temperature controlled enclosure equipped with heating or cooling controls for accurately and precisely controlling and optionally modifying, as a function of time after injection, the temperature experienced by the GC column. The mobile phase or carrier gas flowing through the column causes the components in the gas mixture to elute at different elution times that may be a function of one or more of the carrier gas flow rate, the temperature profile under which the GC oven is operated, and the interactions of the components with the stationary phase of the column. At the elution time previously identified for a component of interest in the sample, the carrier gas exiting the column is diverted into a sample cell of an absorption spectrometer 104. A light beam is passed through the contents of the sample cell 106 and light absorption within the cell is measured 110. The measured absorption is converted to a concentration of the component of interest 112 in the gas mixture. The light beam may optionally be generated by a tunable diode laser which may optionally provide an infrared or near-infrared wavelength.

In general, system valves may be controlled by a process controller or microprocessor programmed to divert gases leaving the GC to the spectrometer sample cell for a time period including the known elution time for the component of interest. In this manner, the component of interest and any possible co-elutants are injected into the sample cell with carrier gas from the GC. The valves are closed once the target species is contained in the spectrometer sample cell. Absorption of the gas contained in the sample cell may be measured by the absorption spectrometer and the concentration of the component of interest in the sample cell calculated based on the absorption as discussed below. The sample cell concentration of the component of interest may be converted to a concentration in the original gas mixture using the following relationships:

$$M_{i,SC} = C_{i,SC} V_{SC} \tag{1}$$

where $M_{i,SC}$ is the mass of trace component i in the sample cell (and also in the sample of the gas mixture injected into the GC column). The concentration of the component of interest in the gas mixture, $C_{i,GM}$ is then $$C_{i,GM} = M_{i,SC}/V_{Inj} \tag{2}$$

where $V_{Inj}$ is the volume of gas injected to the GC column. The stationary phase, carrier gas, temperature profile of the column, and other operating parameters may be selected based on the components of the gas mixture that are to be separated and concentrated.

Figure 2:
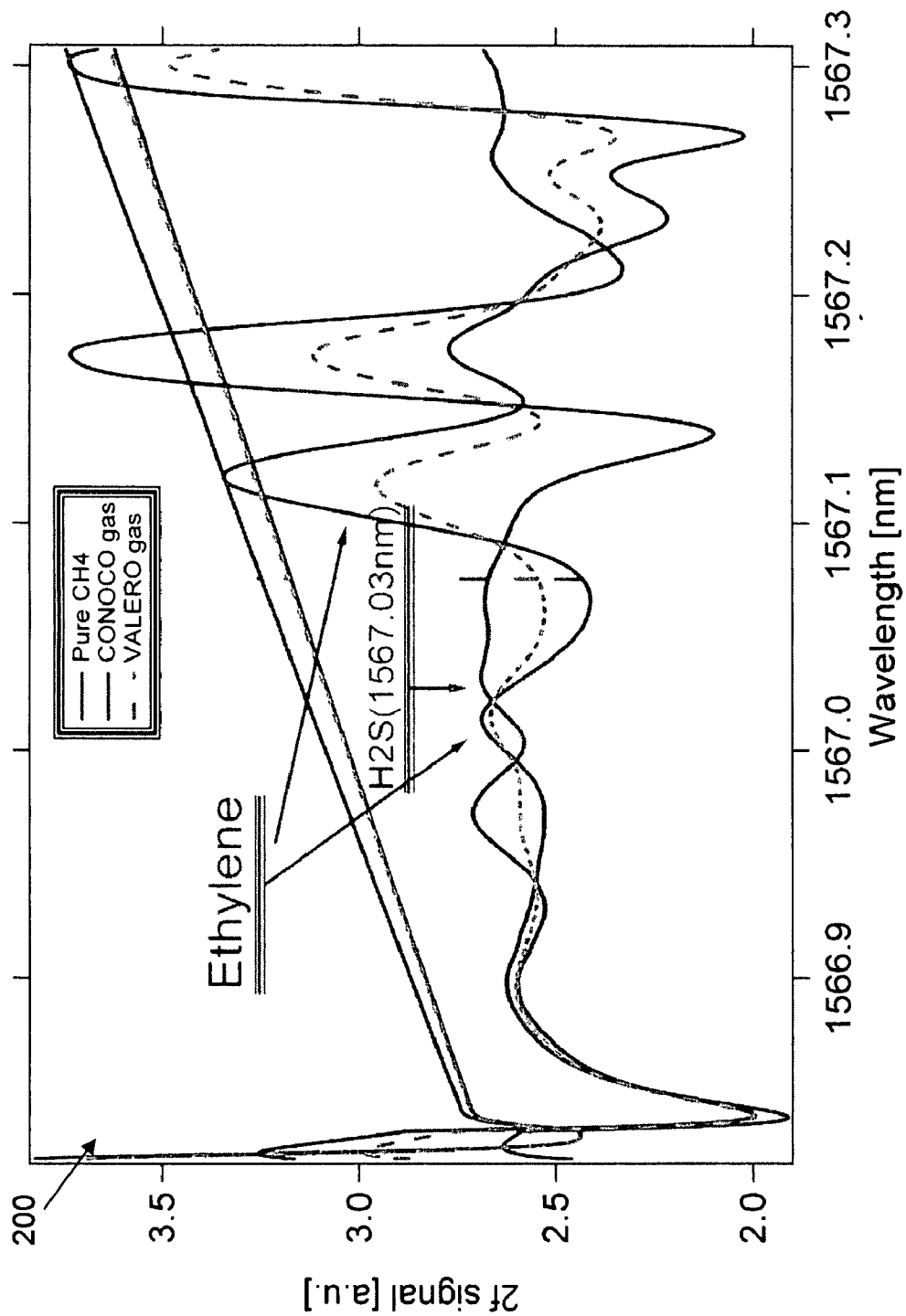
FIG. 2 is a chart showing absorption spectra of hydrogen sulfide, ethylene and methane in gas mixture.
Figure 3:
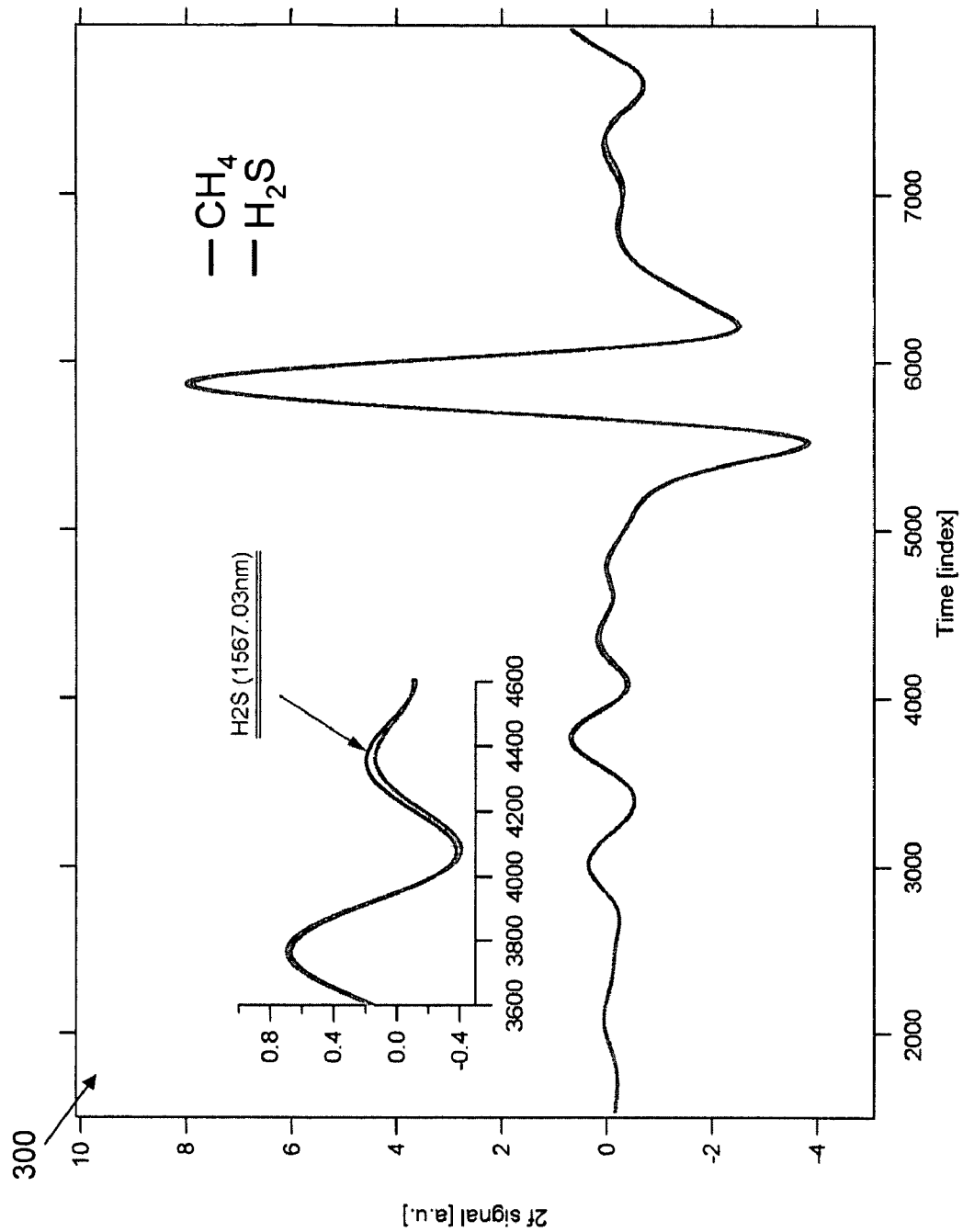
FIG. 3 is a chart showing absorption spectra of hydrogen sulfide and methane in a gas mixture with ethylene removed.

As an example, hydrogen sulfide ($H_2S$) concentrations may be measured in natural gas containing methane ($CH_4$) and ethylene ($C_2H_4$). FIG. 2 is a chart 200 showing absorption spectra in the vicinity of a wavelength of $\lambda=1567$ nm for these three gases. As may be seen from FIG. 2, the absorption spectra of the three gases strongly overlap, particularly at the wavelength of $\lambda=1567.03$ nm, which is the only wavelength in this spectral region for which a tunable diode laser is presently available. Such overlap renders this $H_2S$ absorption line unusable for measurement by conventional absorption spectrometers. In this example, removal of ethylene from a sample of the gas mixture may leave sufficient difference between $CH_4$ and the $H_2S$ absorption spectra permit the use of an absorption spectrometer to measure the $H_2S$ concentration in the gas mixture. FIG. 3 is a chart 300 showing the difference in absorption between $H_2S$ and $CH_4$ near a wavelength of 1567 nm.

Hydrocarbons and many other species found in petrochemical gas mixtures may be analyzed using infrared spectroscopy if a mixture does not contain too many species whose absorption spectra overlap. Near infrared radiation generally lacks sufficient photon energy to induce absorption by electronic transitions such as those induced by ultraviolet radiation. Therefore, IR absorption is restricted to compounds with small energy differences in the possible vibrational and rotational states of the molecules. For a molecule to absorb IR radiation, the vibrations or rotations within a molecule must cause a net change in the dipole moment of the molecule. The alternating electrical field of the radiation interacts with fluctuations in the dipole moment of the molecule. The energy of the incident light radiation is $$E = h\nu \tag{3}$$

where E is the photon energy, h is Planck's constant and ν is the frequency of the light. If E matches the energy necessary to excite a vibrational mode of a molecule, then radiation will be absorbed causing a change in the amplitude of this molecular vibration. The two main types of molecular motion, which includes relative motion between atoms making up the molecule, involve stretching and vibration of inter-atomic bonds.

Stretching transitions require moderate energies and are therefore quite useful to IR absorption spectroscopy. In stretching transitions, the inter-atomic distance changes along bond axes, and the resultant absorbance of IR by gas-phase molecules yield line spectra sufficiently spaced apart to allow detection. In liquids or solids, these lines broaden into a continuum due to molecular collisions and other interactions such that they cannot be measured by IR absorption spectroscopy.

The relative positions of atoms in molecules are not fixed, but are rather subject to a number of different vibrations relative to other atoms in the molecule. A specific molecular motion requires a corresponding quantum of activating photon energy. Therefore, an incident photon's energy must be of exactly the right wavelength to be absorbed into the molecule. Thus, if a gas containing a molecule that absorbs and vibrates at a given wavelength λ is illuminated by a beam of light of wavelength λ, some of the incident photons will be absorbed as it passes through the gas. This absorbance $A_{i,\lambda}$ is calculated from the beam power incident on the sample $P_0$ and the beam power passing through the sample P as follows:

$$A_{i,\lambda} = -\ln(P/P_0) \quad (4)$$

In accordance with Beer-Lambert's Law, the absorbance $A_{i,\lambda}$ due to a specific gas-phase compound i at the incident wavelength λ is directly proportional to its concentration $C_{i,SC}$ in the cell:

$$A_{i,\lambda} = C_{i,SC} \epsilon_{i,\lambda} L \quad (5)$$

where $\epsilon_{i,\lambda}$ is the extinction coefficient for the compound at the incident wavelength, and L is the path length of the absorption/sample cell. If multiple compounds in the sample cell absorb light at the incident wavelength λ, the total absorbance $A_{T,\lambda}$ of the gas mixture in the cell at that wavelength is $$A_{T,\lambda} = L \sum_{i=1}^{n} C_{i,SC} \epsilon_{i,\lambda} \quad (6)$$

As such, the absorbance $A_{i,\lambda}$ of a single compound at the incident wavelength may be extracted from $A_{T,\lambda}$ as follows:

$$A_{i,\lambda} = A_{T,\lambda} - A_{T-I,\lambda} \quad (7)$$

where $A_{T-I,\lambda}$ is the absorbance of the gas mixture with compound i removed.

It will be noted that although this disclosure refers to infrared spectroscopy to illustrate various uses and benefits, other wavelengths may be used to measure gas mixture components with different absorption characteristics.

An analyzer used in connection with the subject matter disclosed here may be used to make measurements of any number of trace gases in other gases or mixtures of gases. The system includes a source of incident light, such as a laser, and one or more absorption spectrometers with sensitivity in the wavelength range of the light source. The spectrometer or spectrometers each include one or more sample cells, arranged such that the gas provides a path length L though which a light beam from the laser source passes before reaching the detector. Control electronics, such as a process controller that may include a microprocessor, and user accessible input/output channels may also be included.

Other implementations of the subject matter described herein include various systems and analyzers for identifying and quantifying the concentration of trace species in complex gas mixtures. One such implementation is illustrated in the schematic diagram of an analyzer 400 shown in FIG. 4 which includes a gas chromatograph (GC) 402 whose output may be routed into an absorption spectrometer 404. Various operational aspects of the system 400 may be controlled by a process controller 406 which may include a microprocessor. The GC may include an oven or other temperature-controlled enclosure 410 that contains a GC column 412 through which a carrier gas moves. The carrier gas is supplied from a carrier gas source 414 which may be a compressed gas cylinder or other comparable source of relatively contaminant-free, inert gas. The GC 402 also includes an injector 416 for delivering a sample of a gas mixture to the GC column 412. Generally, when a sample is not being analyzed, carrier gas flows from the carrier gas source 414 and through the GC column 412.

Figure 5:
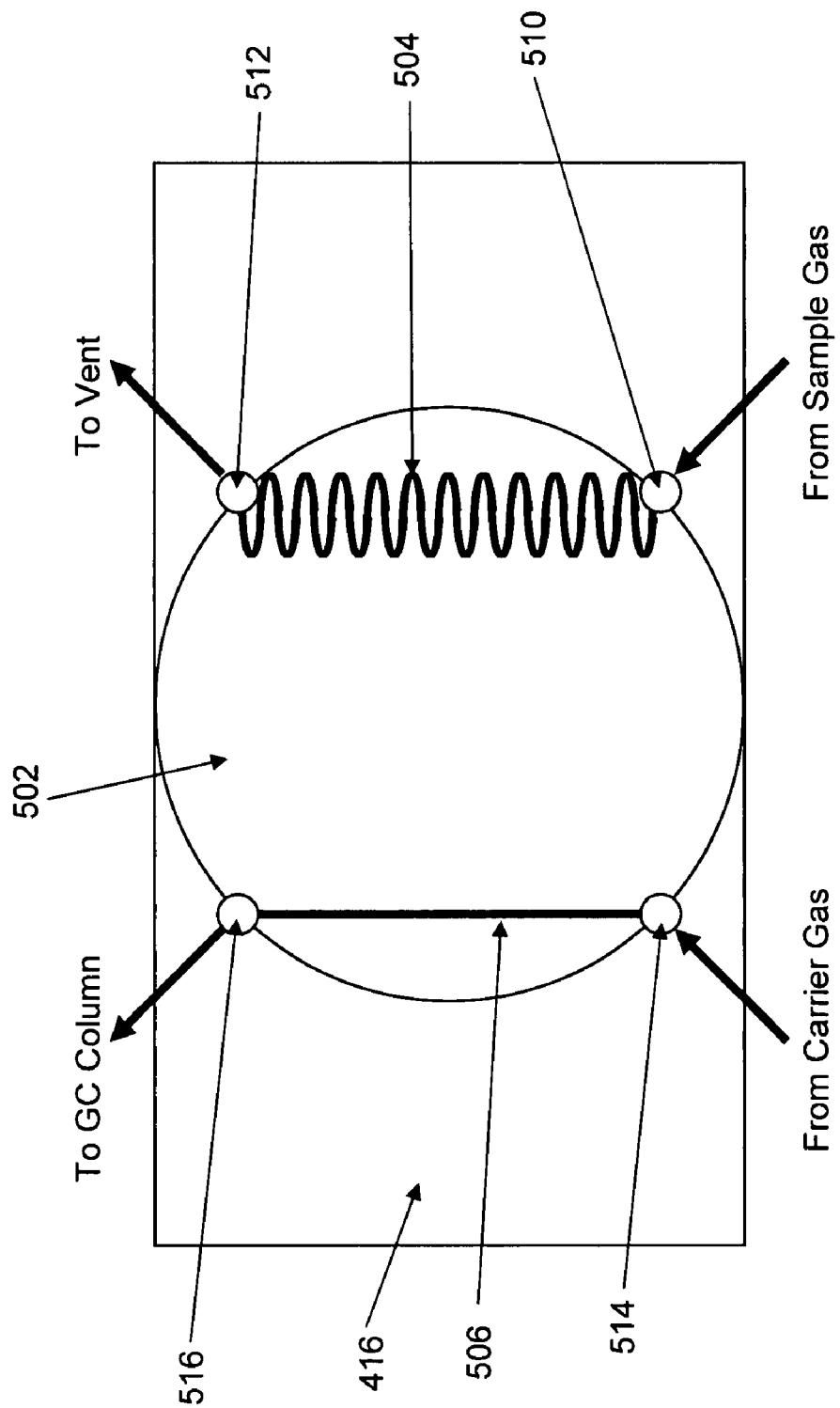
FIG. 5 is a schematic diagram showing a multi-port valve that may be used with the disclosed subject matter.

The injector 416 may take a variety of forms. In one example, the injector 416 may be a simple injection port through which a sample of gas may be injected using a gas syringe or the like. In another example, the injector 416 may include a multi-port valve with a sample loop. An example of an injector 416 that includes a sample loop is shown in FIG. 5. In this example, the injector 416 includes a multi-port valve 502 that includes a sample loop 504 and a bypass connection 506. Prior to injection, the gas mixture to be analyzed flows into a first inlet port 510 on the multi-port valve 502, through the sample loop 504, and out of a vent port 512 on the multi-port valve 502. Flow through the sample loop 504 may be due to positive pressure on the gas mixture side or negative pressure at the vent port 512. Negative pressure may be supplied by a vacuum pump, water aspirator, or any other comparable source of vacuum (not shown). Carrier gas flows into a second inlet port 514 on the multi-port valve 502, through the bypass connection 506, and into the GC column via a column port 516. At the start of sample run, which may be signaled manually or by process controller 406, the multi-port valve rotates, in this example by 180 degrees. Under this arrangement, the sample loop 504 is disposed between the second inlet port 514 and the column port 516 such that carrier gas flows through the sample loop 504 to sweep a known volume of the gas mixture into the GC column for separation and analysis. The bypass connection 506 is disposed between the first inlet port 510 and the vent port 512 to allow continuous flow of the gas mixture. The injector may optionally be maintained at a temperature higher than the boiling points of components expected to be present in the gas mixture to reduce the likelihood of contamination of sequential samples by condensed components from previous sample runs. The injector temperature may also be ramped by the process controller 406. Multi-port valves with different numbers of ports may also be used.

Returning to FIG. 4, once a sample has been injected into the column 412 by the injector 416, the temperature in the temperature-controlled enclosure 410 may optionally be ramped by an oven heater 420 that may be controlled by the process controller 406 according to a predetermined ramp program. Based on calibrations performed under the same temperature-controlled enclosure 410 and injector 416 temperature profiles on samples of the gas mixture or other test gases containing the component of interest, the elution time of the component of interest from the GC column 412 is determined. At or slightly before the predetermined elution time, a GC outlet valve 422 may be actuated. The GC outlet valve 422 may be one or more valves that direct flow exiting the GC column 412. In one example, prior to actuation, the GC outlet valve 422 vents gases exiting the GC column 412 to exhaust. When the GC outlet valve 422 is actuated, gases exiting the GC column 412 are passed into a sample cell 424 of the absorption spectrometer 404. Once a sufficient time has passed to deliver a substantial fraction of the component of interest exiting the GC column 412, the GC outlet valve 422 may be de-actuated to close the inlet to the sample cell 424 and thereby prevent dilution and/or contamination of the component of interest in the sample cell. A sample cell flush inlet valve 426 and sample cell flush outlet valve 430 may also be provided to clear the sample cell between samples. In the example where these additional valves are included, the sample cell flush inlet valve 426 may be closed when the GC outlet valve 422 is actuated. The sample cell flush outlet valve 430 may be closed when the GC outlet valve 422 is de-actuated. The GC outlet valve 422 and sample cell flush inlet valve 426 and outlet valve 430 may be controlled by the process controller 406 according to a predetermined sequence based on the expected elution time of the component of interest.

Once the component of interest is contained within the sample cell 424, an absorption spectrum of the gas in the sample cell 424 is obtained by passing a light beam 432 from a laser source 424 through the gas contained in the sample cell 424. After the beam traverses the sample cell 424, it impinges upon a photodetector 436 which quantifies light that is transmitted through the gas contained in the sample cell. The light beam 432 from the laser source 434 may optionally enter the sample cell 424 through an input window (not shown) and exit the cell though an exit window (not shown) prior to being detected by the photo detector 436. The resulting absorption spectrum may be recorded by the process controller 406 or some other microprocessor system to determined the concentration of the component of interest in the sample cell, and also in the gas mixture itself. To account for detector drift and other potential measurement artifacts, an absorption spectrum for the sample cell filled with only the flush gas may be periodically recorded to determine the dark current "zero" of the photodetector 436.

The presently disclosed subject matter may also be used to measure more than one trace component of a gas mixture using a single sample injection to the injector 416. For analysis of multiple components, the elution times of the components should be sufficiently spaced to allow a first component's absorption spectrum to be measured and the sample cell 424 to be flushed before a second component elutes. The injector 416 and/or temperature-controlled enclosure 410 temperature profiles may be modified or a different column and/or carrier gas flow rate may be used as necessary to provide a sufficient delay between the elution times of two components of a gas mixture. Alternatively, more than one absorption spectrometer may be connected to the output of a GC column with a first absorption spectrometer being used to analyze a first eluting component and a second absorption spectrometer being used to analyze a second eluting component.

Figure 6:
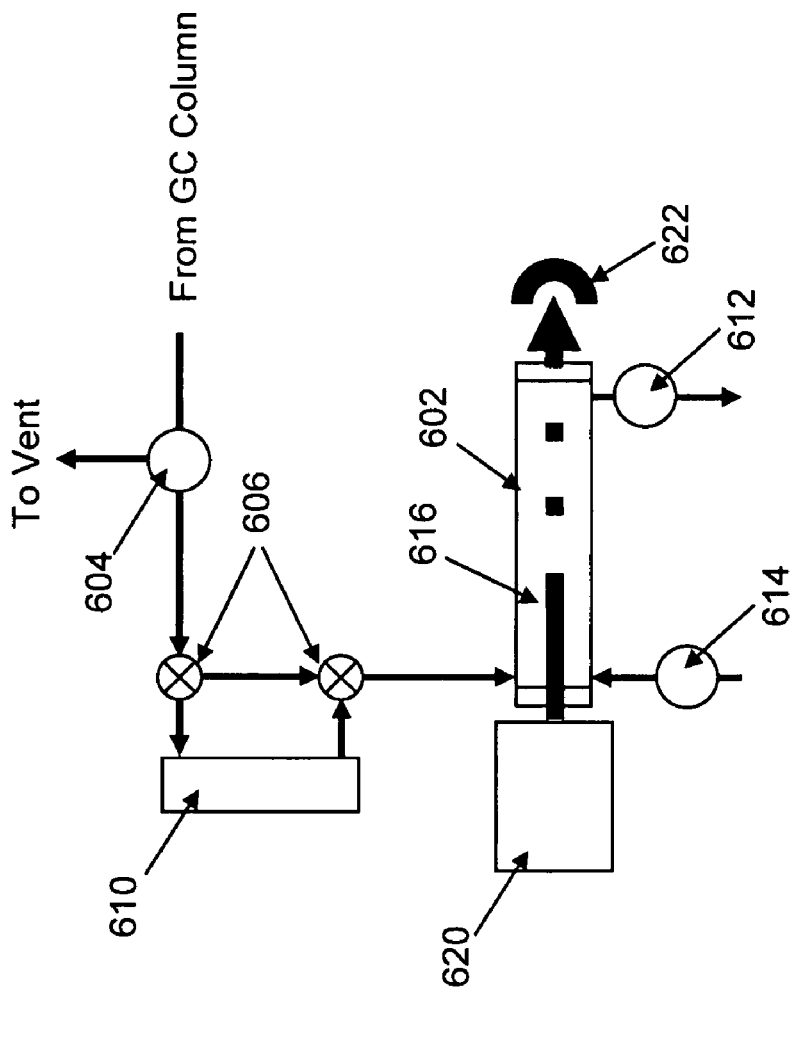
FIG. 6 is a schematic diagram showing a second trace gas analyzer that features differential absorption spectroscopy.

In some cases, it may not be possible to completely separate the components of a gas mixture using a GC column. In this case, more than one component may be delivered to the sample cell 424 shown in FIG. 4 during the time period between actuation and de-actuation of the GC outlet valve 422. If the gas mixture components that co-elute in this manner also have overlapping absorption features, it may be necessary to employ a differential spectroscopy technique as is described in co-pending U.S. patent application No. 11/715, 599, the contents of which are hereby fully incorporated by reference. FIG. 6 shows an illustrative implementation of the absorption spectrometer portion of an analyzer that uses this additional technique to resolve the concentration of a component of interest. Two sequential samples of the gas mixture are separated and concentrated by a GC column and then analyzed in the absorption spectrometer.

FIG. 6 depicts part of an implementation featuring an analyzer 600 that may be used to perform differential absorption spectroscopy in conjunction with GC separation of components in a gas mixture. Absorption of the contents of the sample cell 602 is measured for sequential samples injected into a GC column (not shown) via an injector (not shown) as discussed above in conjunction with FIG. 4. For the first injected sample, when the GC outlet valve 604 is actuated to direct the component of interest to the sample cell 602, one or more scrubber valves 606 are positioned to pass the gas exiting the GC column through a scrubber 610 before the gas enters the sample cell 602. The scrubber 610 reduces the concentration the component of interest in the gas that is passed to the sample cell 602. The GC outlet valve 604 and sample cell flush outlet valve 612 are closed and a background absorption spectrum is measured by passing a light beam 616 generated by a laser source 620 through the gas contained in the sample cell 602 to a photodetector 622. The sample cell 602 is then flushed by opening the sample cell flush inlet valve 614 and the sample cell flush outlet valve 612 to pass carrier gas through the sample cell 602 to prepare it for the second injected sample.

For the second injected sample, when the GC outlet valve 604 is actuated, the sample cell 614 flush 614 is closed and the scrubber valve or valves 606 direct the gas exiting the GC column directly into the sample cell 602. The GC outlet valve 604 and sample cell flush outlet valve 612 are closed and an unscrubbed absorption spectrum is measured for the second sample by passing a light beam 616 generated by a laser source 620 through the gas contained in the sample cell 602 to a photodetector 622. This unscrubbed sample does not pass through the scrubber 610, so the absorption measured in the sample cell 602 reflects the absorption of both the component of interest and the other, potentially interfering species that may have co-eluted from the GC column with the component of interest. A microprocessor, which could be the process controller (not shown) calculates the absorption due to the component of interest by calculating and analyzing a differential absorption spectrum using the background and unscrubbed spectra collected for the first and second samples, respectively.

Figure 7:
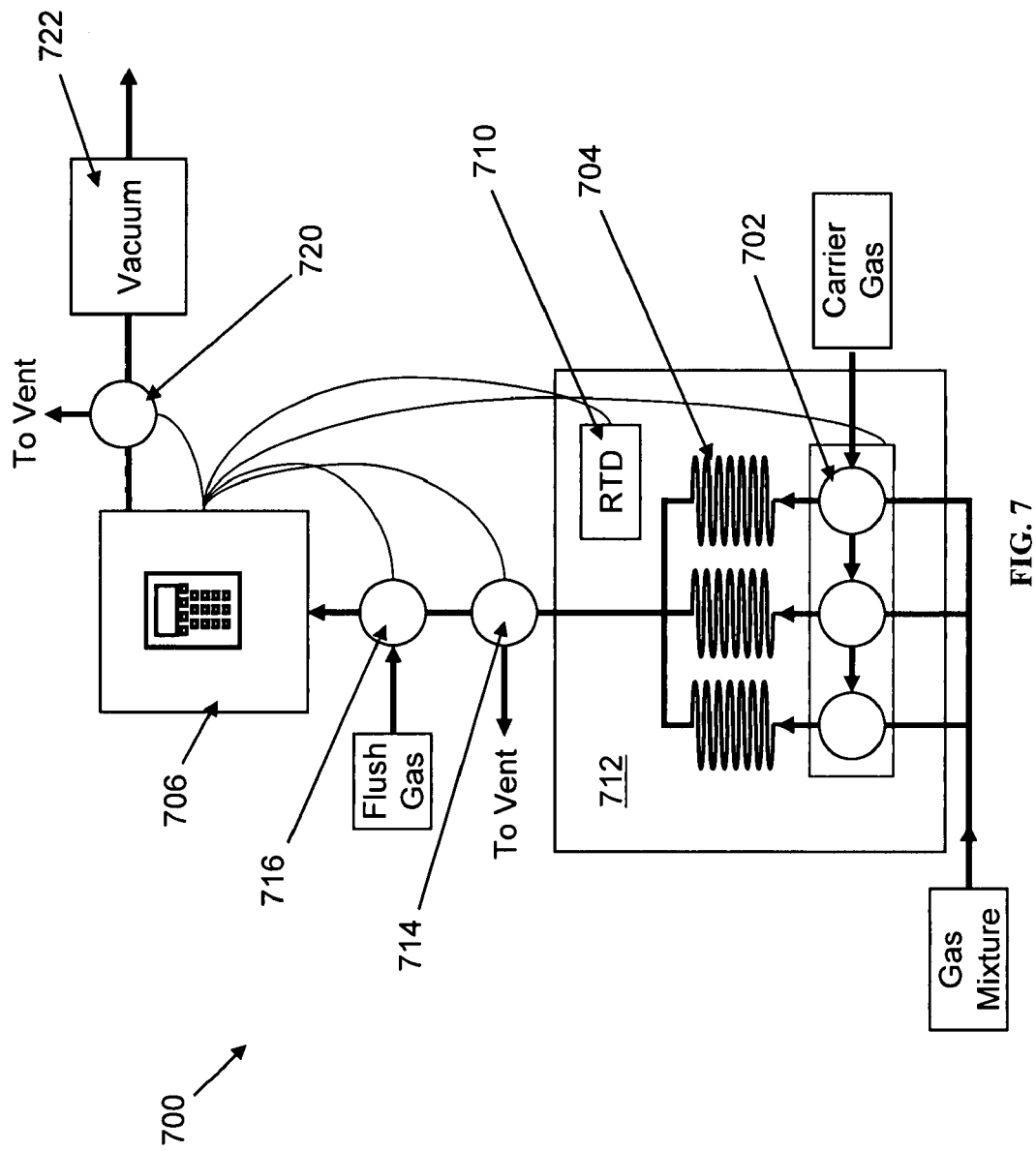
FIG. 7 is a schematic diagram showing a third trace gas analyzer that features multiple GC columns.

In another implementation, a gas chromatograph with multiple columns may be used to increase the mass of the component of interest delivered to the absorption spectrometer. An example of such an analyzer 700 is depicted schematically in FIG. 7. The gas mixture is introduced to such an analyzer through multiple injectors 702 each of which delivers a volume of the gas mixture to one of a set of multiple GC columns. The analyzer 700 shown in FIG. 7 features three columns, but any number of columns is within the scope of the present subject matter. For very low concentrations of the component of interest in the gas mixture, a very long absorption pathlength may be required so that the absorption spectrometer 706 can accurately detect and quantify the component. Larger amounts of the gas mixture may be separated by gas chromatography to provide a sufficient concentration of the component of interest in a larger sample cell of the absorption spectrometer 706. The number of GC columns 704 and injectors 702 used may depend on the absorption characteristics of the component of interest and its concentration in the gas mixture. For example, if approximately 4.3 in$^3$ (71 cm$^3$) of the gas mixture is required to provide sufficient mass of the component of interest to give a quantifiable sample cell concentration for absorption and a single GC column and injector is capable of separating a gas mixture sample volume of no more than approximately 15 cm$^3$, four or even five GC columns 704 and injectors 702 may be used to supply an adequate mass of the component of interest in the sample cell (not shown) of the absorption spectrometer 706.

In operation, the temperature from a temperature measurement device 710, which may be a resistance device such as a thermocouple, located in a temperature-controlled enclosure or oven 712 containing the GC columns 704 may be monitored for a preset period, for example approximately 10 seconds, to determine the average temperature of the temperature-controlled enclosure 712. Once the average temperature of the temperature-controlled enclosure 712 has been determined, electronics associated with the absorption spectrometer 706 are used to determine the actual valve time off time for the injectors 702 and the appropriate valve times for a GC outlet valve 714, a spectrometer input valve 716, and a spectrometer outlet valve 720, each of which may be a three-way valve. Prior to analysis of a gas mixture sample, the GC outlet valve 714 is set to vent gas exiting the GC columns 704. The spectrometer input valve 716, is open to the atmosphere or a flush gas source. The spectrometer outlet valve 720 is opened to a vacuum pump 722 or other source of negative pressure that causes clean air or the flush gas to be drawn through the sample cell of the absorption spectrometer 706.

The injectors 702 are opened at an initial time To and a gas sample is introduced into the GC columns 704. Based on a prior knowledge of the time for the target gas molecule to be emitted from the GC columns 704, the spectrometer inlet valve 712 is closed to atmosphere or flush gas source and routes the target gas to the absorption spectrometer 706. As noted above, the spectrometer inlet valve 712 remains open for a sufficient period to allow the component of interest to elute from the GC columns 704 and pass into the sample cell of the absorption spectrometer 706. Once the component of interest has finished eluting form the GC columns 704, the GC outlet valve 710 switches back to vent to allow other, unmeasured, components of the gas mixture to bypass the sample cell of the absorption spectrometer. When the GC outlet valve 714 switches back to vent, the spectrometer outlet valve 720 and optionally the GC inlet valve 716 may close to capture a static volume of gas containing the component of interest in the sample cell of the absorption spectrometer 706.

Absorption of light is measured by the absorption spectrometer 706 as discussed above in conjunction with FIG. 4. This measurement is then compared to a calibration matrix for pressure, temperature and the degree of concentration of the component of interest in the GC columns relative to its concentration in the gas mixture itself. These data may be computed in a microprocessor or other electronics associated with the absorption spectrometer 706. The resultant calibrated concentration of the component of interest in the gas mixture may be sent to absorption spectrometer outputs, for example via a 4-20 mA current loop or a RS-232 serial port. Once the measurement is complete, the spectrometer outlet valve 720 is opened to the vacuum pump 722 and the spectrometer input valve 716 is opened to the atmosphere or the flush gas source to clear the sample cell of the absorption spectrometer 706 and keep it dry. When the sample cell has been cleared, the cycle starts again with the injection of another sample of the gas mixture into the GC columns 704. Automatic determination of gas chromatograph valve activation times based on a temperature versus time matrix provides the benefit of nearly automated sample collection, analysis, and recovery of the system for analysis of the next sample.

Figure 4:
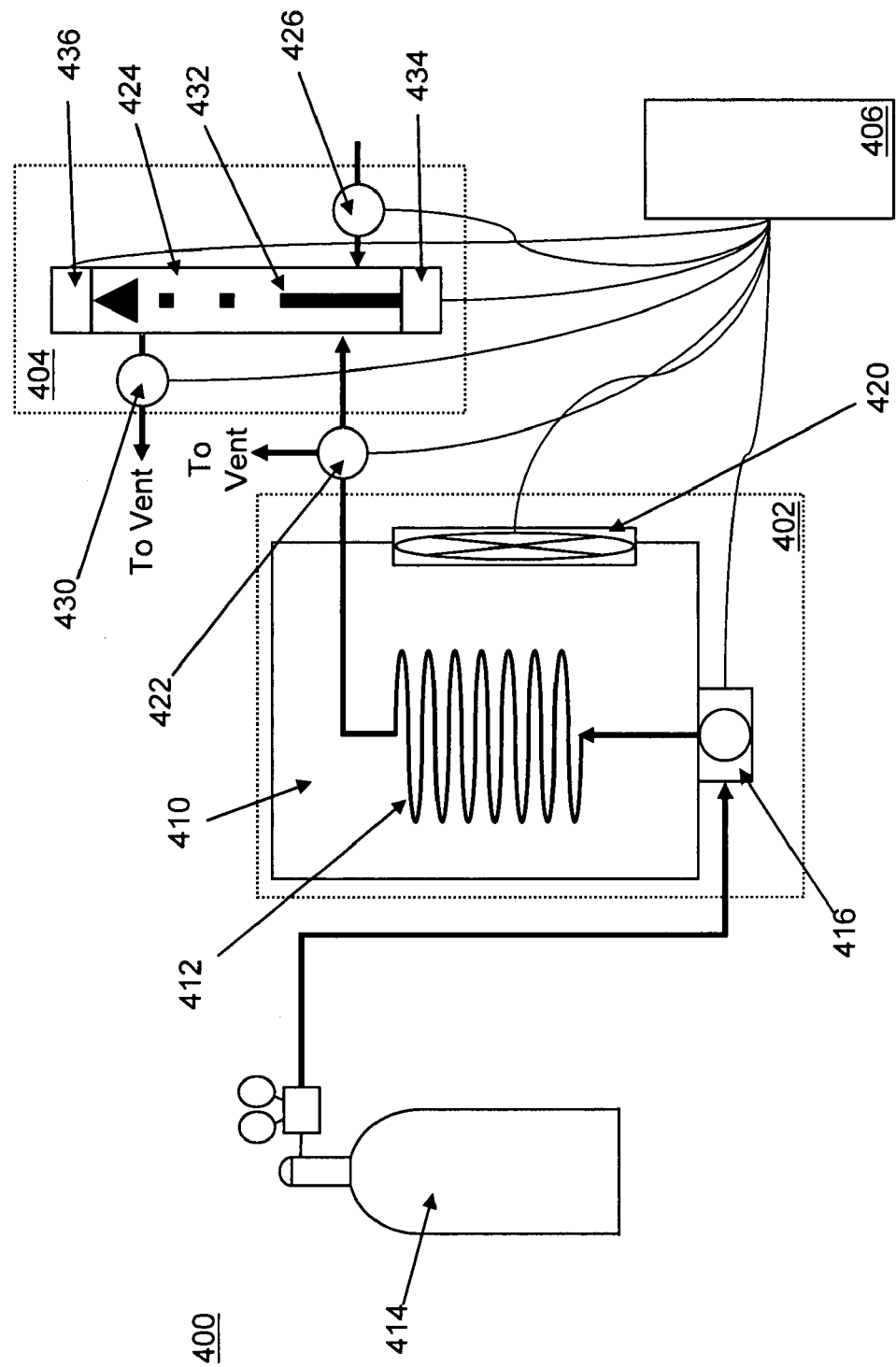
FIG. 4 is a schematic diagram showing a first trace gas analyzer.

The example implementations shown in FIG. 4 and FIG. 6 depict absorption spectrometers with single pass sample cells in which the light beam traverses the gas in the sample cell once on the way from the laser source to the photodetector. In some cases, the concentration of the component of interest in the sample cell may be very small or not readily distinguishable from other components that could not be readily separated by the GC column. In such cases, the length of the cell may be increased to increase the sensitivity of the measurement. As equation 5 states, $A_{i,\lambda}$ is directly proportional to the path length L over which the laser beam traverses the gas in the sample cell. Thus, a cell that is twice as long will absorb twice as much light etc. Therefore, in some implementations of the analyzers described herein, sample cells are employed that have path lengths on the order of many meters or even thousands of meters.

To achieve longer optical path lengths without the use of extremely long sample cells, sample cell configurations within the scope of this disclosure may also include the use of one or more mirrors to reflect the beam such that the beam passes through the sample contained in the sample cell two or more times. In such a multi-pass configuration, the beam may enter and exit the cell through the same window or through different windows. In some implementations, windowless sample cell configurations may be utilized in which, for example, the laser source and/or the photodetector are contained within the sample cell.

Figure 8:
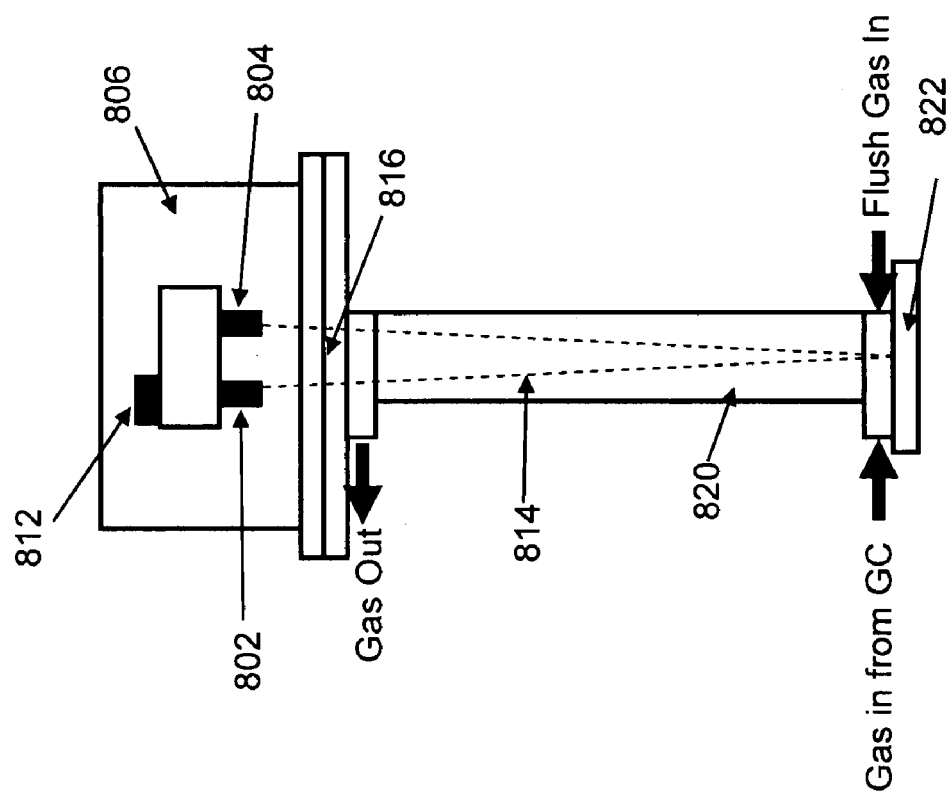
FIG. 8 is a schematic diagram showing a multi-pass absorption spectrometer.

One example of such a multi-pass sample cell configuration is shown in FIG. 8, which depicts a two-pass sample cell and laser/detector head 800. A laser 802 and photodetector 804 are positioned in an optical head 806 mounted to a baseplate 810 whose temperature is controlled by a thermoelectric cooler (TEC) 812. The incident laser light 814 is directed out of the optical head 806 through a window 816 into the sample cell 820. The light travels the length of the sample cell 820 twice as it is reflected at the far end of the cell by a flat mirror 822. The returning light is transmitted back through the window 816 and impinges on the photodetector 804.

Figure 9:
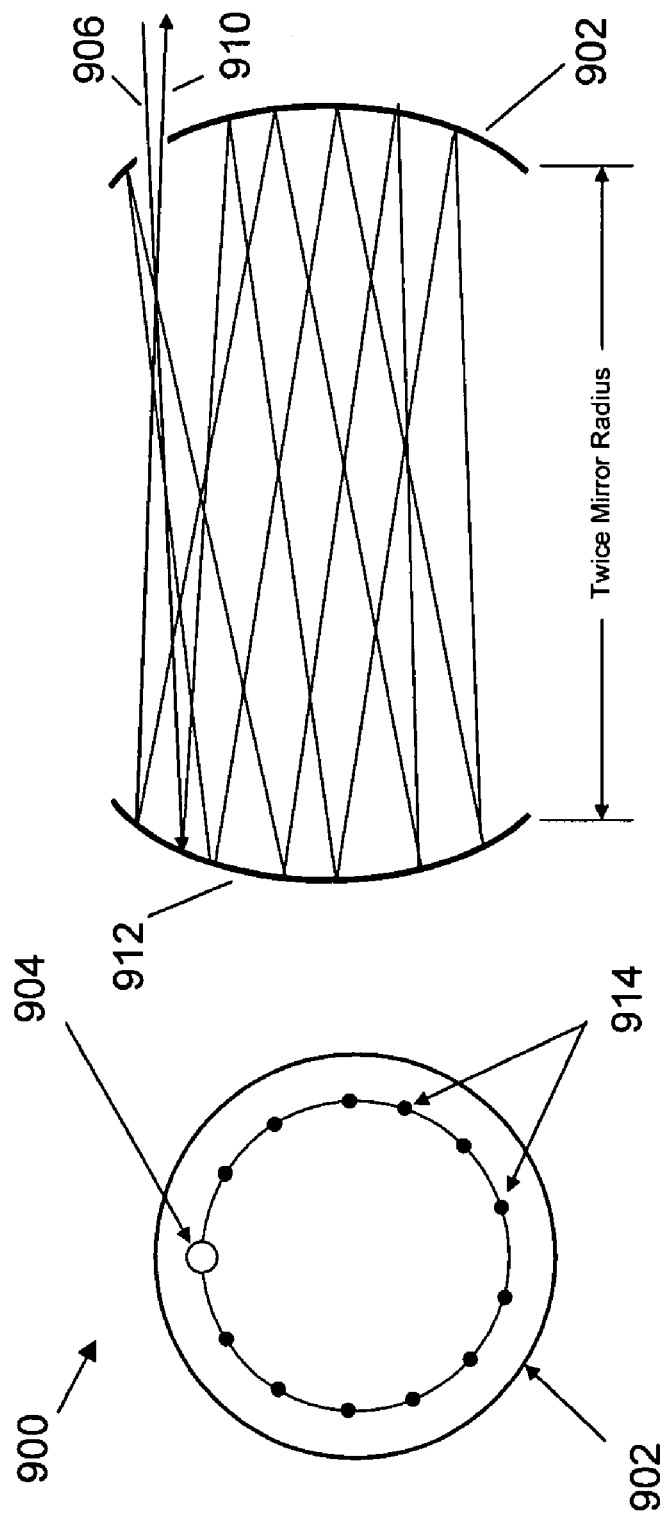
FIG. 9 is a schematic diagram showing a multi-pass absorption spectrometer sample cell.

Longer effective pathlengths may also be achieved by using an off-axis resonating cavity which includes two highly reflective mirrors. These sample cells, which are also referred to as Herriot cells, are variants of cavity ring down spectrometers that are called integrated cavity output spectrometers (ICOS). An schematic diagram 900 of a Herriot cell is shown in FIG. 9. These long cells may also be used to make these very sensitive measurements using either direct absorption or "2 f" detection as discussed in more detail below. The front view of one such mirror 902 shows an input/output aperture 904 for allowing the light beam to enter 906 the cell and then exit 910 the cell on the way to the photodetector (not shown). The opposite mirror in such a cell 912 in this cell does not have an aperture. An alternative configuration of a Herriot cell includes an aperture in each of the facing mirrors such that the beam enters through an aperture in one mirror and exits the cell through an aperture in the other mirror. The end mirror 902 shown in FIG. 9 also illustrates how the laser beam contact points 914 on the mirror 902 are arranged in a circle such that the beam does not interfere with itself as it is relayed back and forth between two such mirrors.

Herriott cells may be designed for a broad number of cell lengths but tend to have an upper bound that depends on the reflectance of the mirrors. If the reflectance of the mirrors at the operating wavelength is not very high, the incident light beam rapidly loses intensity as it traverses back and forth between the mirrors. For example, for a mirror reflectance of 98%, the intensity of light reaching the photodetector after 70 passes is $0.98^{70}$ or only 24.3% of that when the beam enters the cell. If this light is further attenuated by absorption by gas molecules in the cell, the amount actually reaching the photodetector may be quite small.

Additional information about Herriot cells and general background information on their use in absorption spectroscopy may be found in the following references, each of which is incorporated by reference in its entirety: D. Herriott, H. Kogelnik and R. Kompfner, "Off Axis Paths in Spherical Mirror Interferometers," *Applied Optics*, Vol. 3, No. 4, 1964; Donald R. Herriott and Harry J. Schulte, "Folded Optical Delay Lines," *Applied Optics*, Vol. 4, No. 8, 1965; Alphan Sennaroglu and James G. Fugimoto, "Design Criteria for Herriott-type Multi-pass Cavities for Ultrashort Pulse Lasers," *Optics Express*, Vol. 11, No. 9, 2003; and Jean Francois Doussin, Ritz Dominique and Carlier Patrick, "Multiple-pass Cell for Very-long-path Infrared Spectrometry," *Applied Optics*, Vol. 38, No. 19, 1999.

The light source used for the absorption measurements disclosed may emit in the infrared (for example in a wavelength range of approximately 800 to 10,000 nm). The analyzer may utilize a laser whose spectral bandwidth is much narrower than the bandwidth of the absorption lines of interest. Such an arrangement allows for single line absorption spectroscopy in which it is not necessary to scan the entire width of the absorption line or even the peak absorption feature of the line. The wavelength of the laser may be chosen to be one at which there is a resolvable difference in the relative absorbance of water molecules and the other components of the gas to be measured. In one implementation, the laser frequency may be scanned (tuned) back and forth across the chosen absorption wavelength while a photodetector positioned at the opposite end of the beam path length quantifies the light intensity transmitted through the sample as a function of wavelength.

A tunable diode laser (TDL) may be employed as the laser source for the disclosed analyzers. Examples of tunable lasers that may be used are the distributed feedback laser (DFB), the vertical cavity surface emitting laser (VCSEL), and the horizontal cavity surface emitting laser (HCSEL). These lasers can be direct emitters or fiber coupled. Quantum cascade lasers may also be utilized as can other lasers capable of producing a beam of incident light in the desired wavelength range.

DFB Lasers employ a distributed Bragg grating etched onto the active layer of a semiconductor laser which locks the central wavelength within the gain band. As such, only a single longitudinal mode is pumped from the available energy. This optical structure is sensitive to refractive index variations due to carrier density (more or less proportional to the current applied at the junction) and temperature. When laser current and laser temperature are accurately controlled, the peak wavelength can be tuned accurately along a useful range. The control using current is fast, but the sensitivity to the central frequency is weak, typically on the order of 0.01 nm/mA. This sensitivity is weak for large tuning distances, but is strong enough to obtain a flat output power while tuning wavelength by changing the temperature. Thermal stabilization time for a standard DFB module is relatively slow, on the order of a few seconds, which makes this type of controlled source more appropriate for fixed temperature, controlled current applications.

A VCSEL is a type of semiconductor laser diode whose laser beam is emitted perpendicular to the wafer chip surface, in contrast to conventional edge-emitting semiconductor lasers which emit from surfaces formed by cleaving the individual chip out of a wafer. The laser resonator includes two distributed Bragg reflector (DBR) mirrors parallel to the wafer surface with an active region consisting of one or more quantum wells for the laser light generation in between. The planar DBR-mirrors consist of layers with alternating high and low refractive indices. Each layer has a thickness of a quarter of the laser wavelength in the material, yielding an intensity reflectivity above 99%. High reflectivity mirrors are required in VCSELs to balance the short axial length of the gain region. In some VCSELs the upper and lower mirrors are doped as p-type and n-type materials, forming a diode junction. In more complex structures, the p-type and n-type regions may be buried between the mirrors, requiring a more complex semiconductor process to make electrical contact to the active region, but eliminating electrical power loss in the DBR structure. VCSELs for wavelengths from 650 nm to 1300 nm are typically based on gallium arsenide (GaAs) wafers with DBRs formed from GaAs and aluminum gallium arsenide. Longer wavelength devices, from 1300 nm to 2000 nm, have been made with at least the active region made of indium phosphide.

A horizontal-cavity surface-emitting laser (HCSEL) combines the power and high reliability of an edge-emitting laser with the low cost and ease of packaging of a vertical cavity surface-emitting laser (VCSEL). The HCSEL is a semiconductor laser with an elongated cavity that is fabricated on a substrate by etching a 45° angled facet at the emitter end and a 90° facet at the back end of the cavity. The rear reflective region can incorporate an etched distributed Bragg reflector next to the rear facet. Dielectric coatings may be used for reflectivity control.

Quantum Cascade Lasers (QCL) are semiconductor lasers that rely on transitions within several quantum wells that normally emit in the mid-infrared spectral region. QCLs operate on laser transitions not between different electronic bands but on intra quantum well transitions of a semiconductor structure. By using a multitude of quantum wells in a series, a higher optical gain is achieved. Transition energies are defined not by fixed material properties but rather by design parameters (particularly by layer thickness values of quantum wells). As such, QCLs can be designed for operational wavelengths ranging from a few microns to well above 10 microns. High efficiencies may be achieved using a cascade of laser transitions, where a single electron can generate dozens of mid-infrared photons. Continuously operating room-temperature devices are normally limited to moderate output power levels of a few milliwatts.

With the laser absorption spectrometers described herein, the tunable laser wavelength may be varied by changing the injection current while keeping the laser temperature constant. The temperature may be controlled by placing the laser in intimate contact with a thermoelectric cooler (Peltier cooler) whose temperature is measured with a thermistor and controlled by a feedback circuit.

In some implementations, an absorption spectrometer system may employ a harmonic spectroscopy technique in connection with its TDL light source. Harmonic spectroscopy as used in the disclosed subject matter involves the modulation of the TDL laser (DFB or VCSEL) wavelength at a high frequency (kHz-MHz) and the detection of the signal at a multiple of the modulation frequency. If the detection is performed at twice the modulation frequency, the term second harmonic or "2 f" spectroscopy is used. Advantages to this technique include the minimization of 1/f noise, and the removal of the sloping baseline that is present on TDL spectra (due to the fact that the laser output power increases as the laser injection current increases, and changing the laser injection current is how the laser is tuned).

Figure 10:
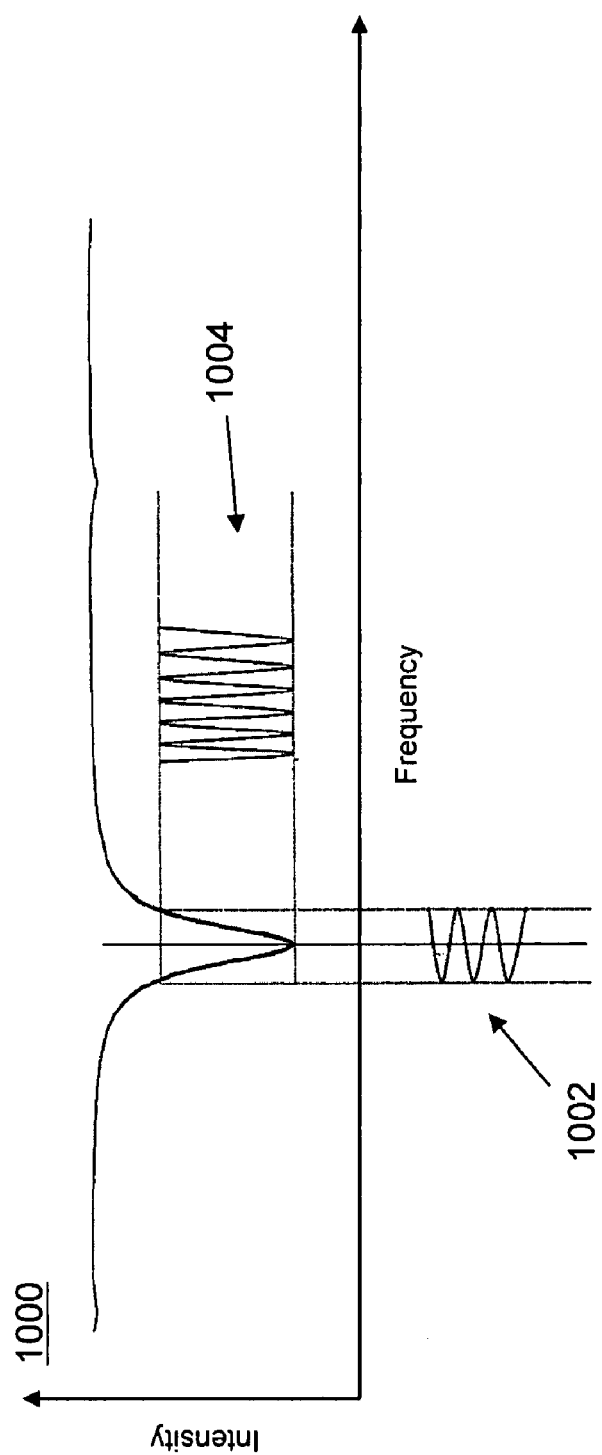
FIG. 10 is a chart that illustrates principles of wavelength modulation spectroscopy.
Figure 11:
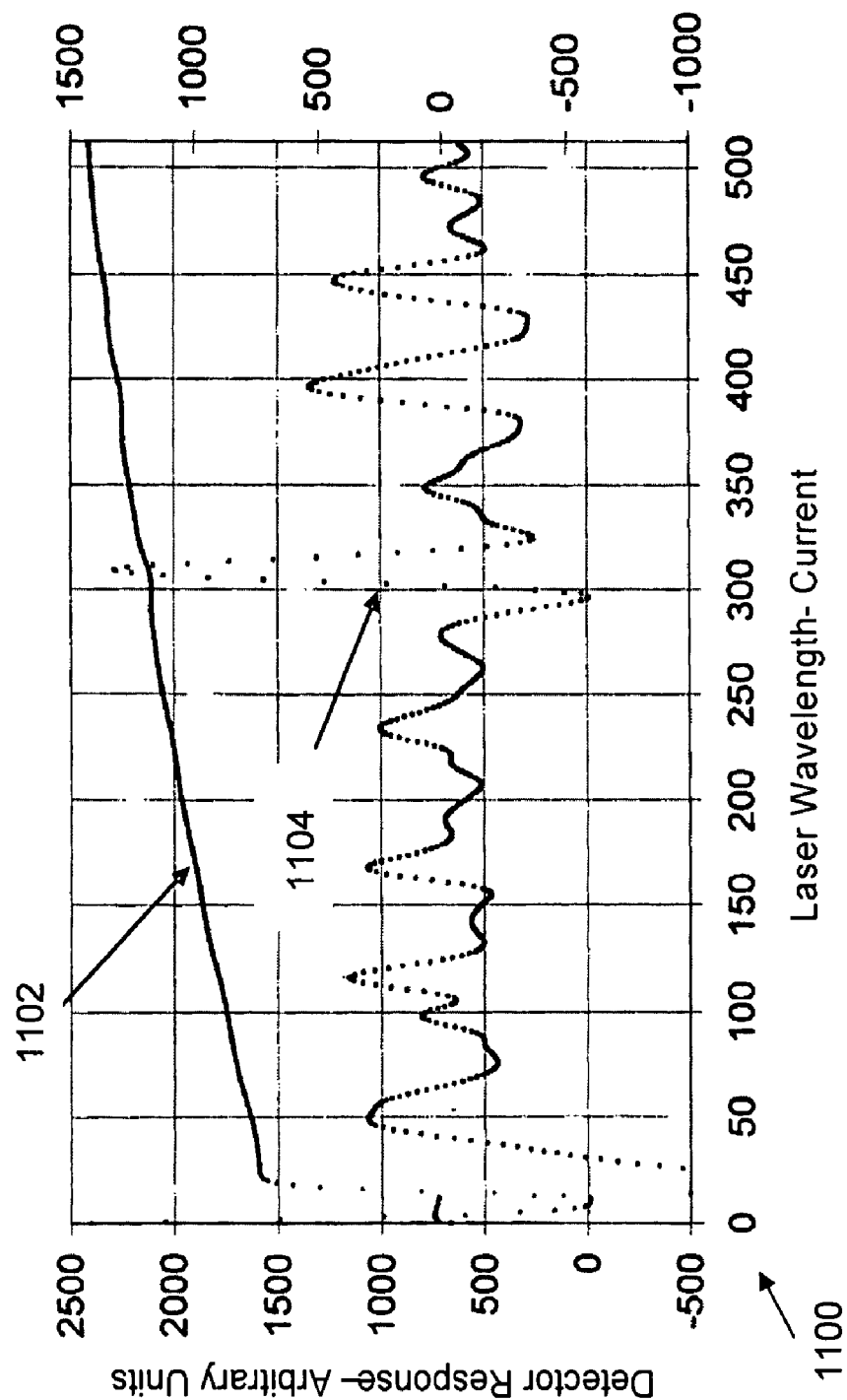
FIG. 11 is a chart showing an example of a laser current drive signal.

FIG. 10 shows an example of a laser scan 1000 for use in harmonic spectroscopy. A combination of a slow ramp and a fast sinusoidal modulation 1002 is used to drive the diode laser. The photodetector receives this modulated intensity signal. The $N^{th}$ harmonic component is resolved by demodulating the received signal. Detection using the signal at the second harmonic (2 f) may be used. The 2 f lineshape is symmetric and peaks at line center due to the nature of even function. Additionally, the second harmonic (2 f) provides the strongest signal of the even-numbered harmonics. FIG. 11 presents a chart 1100 of a typical laser intensity signal (DC) 1102 and 2 f lineshape 1104 vs. frequency. By shifting detection to higher frequency, 2 f spectroscopy can significantly reduce 1/f noise thus provides a substantial sensitivity enhancement compared to direct absorption methods.

In another implementation, direct absorption spectroscopy may be used. In this implementation, the laser frequency is tuned over the selected absorption transition and the zero-absorption baseline may be obtained by fitting the regions outside the absorption line to a low-order polynomial. The integrated absorbance is directly proportional to the concentrations of absorbing species in the laser pathlength as well as the line strength of the transition. The absolute species concentration may be obtained without any calibration.

Photodetectors used in the analyzers disclosed herein depend on the specific wavelengths of the lasers and absorption lines to be measured. For infrared and near-infrared absorption spectroscopy, one potential photodetector is an indium gallium arsenide (InGaAs) photodiode sensitive to light in the 1200 to 2600 nm wavelength region. For longer wavelengths, an indium arsenide photodiode, sensitive for wavelengths up to approximately 3.6 µm, may be used. Alternatively, indium antimonide detectors are currently available for wavelengths as long as approximately 5.5 µm. Both of the indium devices operate in a photovoltaic mode and do not require a bias current for operation. These photodetectors, which lack low frequency noise, are advantageous for DC or low frequency applications. Such detectors are also advantageous for high speed pulse laser detection, making them particularly useful in trace gas absorption spectroscopy.

An analyzer may be controlled by a process controller or a microprocessor that controls the laser current and synchronizes the laser current drive with the signal recording to facilitate detection of very low level signals. The detector signal processing and input/output to the user and data recording may be provided through direct interfaces with the microprocessor.

Figure 12:
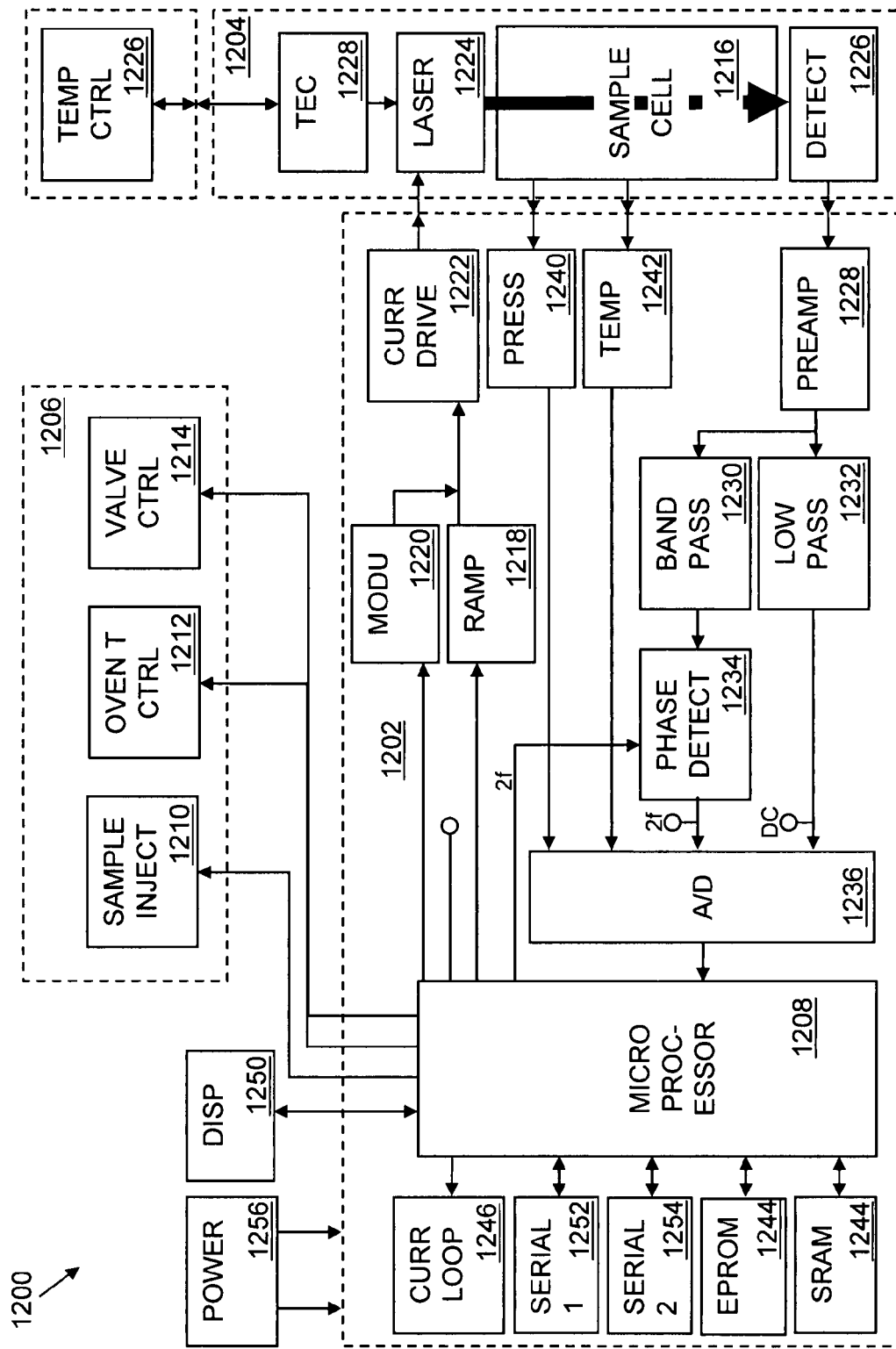
FIG. 12 is a block diagram of a measurement system for analyzing trace gas concentrations.

FIG. 12 is a diagram of an analyzer system 1200 that includes a control and data processing loop system with a process controller 1202 in communication with a spectrometer 1204 and a gas chromatograph (GC) 1206. The process controller includes microprocessor 1208 which directs and coordinates analyzer functions and actions. At the start of an analysis run for a sample of the gas mixture, the microprocessor signals the sample injector 1210 of the GC to inject the sample into the GC column. As the GC run progresses, the microprocessor may control a GC oven temperature controller 1212 to ramp the temperature inside the temperature controlled enclosure in which the GC column is operated. At or slightly before the pre-determined elution time for the component of interest in the gas mixture, the microprocessor 1208 signals a GC valve controller 1214 or controllers to operate one or more valves to direct the gas exiting the GC column into the sample cell 1216 of the absorption spectrometer 1204.

Once the component of interest is contained within the sample cell 1216, a signal is generated by the microprocessor 1208 in the form of a rectangular pulse. This pulse is generated periodically. In one implementation, a 263 msec wide pulse is generated every 0.25 seconds. Other pulse widths and generation frequencies may be utilized. Each pulse is directed toward a ramp generator 1218 that creates a DC signal, an example of which is shown diagrammatically in FIG. 11. In addition to the ramp signal, a modulating sine wave, at for example 7.5 KHz, may be imposed on the current ramp by a modulator 1220 for later use in small signal detection. This combined signal is directed to the laser current driver 1222 and on to the laser 1224 itself.

In this implementation, the laser temperature is held constant by a temperature controller board 1226 and the current varied for tuning the laser wavelength. The temperature control loop uses a thermistor (not shown) located close to the laser 1224 as the temperature input and a thermoelectric cooler 1228 mounted as thermally close to the laser 1224 as possible. TECs and thermistors may be positioned either directly adjacent to the laser diode or externally to the laser diode enclosure. The temperature controller 1226 may be used to set the exact laser wavelength such that variation of the driving current may provide the tuning range which may, for example, be in the range of approximately ±0.3 cm$^{-1}$.

At the beginning an absorption measurement cycle, the current is held to zero to read the signal produced by the photodetector 1226 without laser input and thereby provide the zero for that measurement cycle. This zero may vary a small amount due to slight changes in the photodetector dark current and the electronic noise so it is advantageous to measure it during each photodetector cycle. Following determination of the zero, the current is rapidly increased to the laser threshold current. This current is then increased over the remainder of the cycle until the peak current is reached. The beam created from this signal is directed through the sample cell 1216 and onto the photodetector 1226 which may be a photodiode array or other comparable detector. The output current from the photodetector is first amplified by a preamplifier 1228. The output of the preamplifier is split and sent to a bandpass filter 1230 and a lowpass filter 1232. The bandpass filter 1230 is a narrowband filter that singles out the 2 f signal at 15 KHz and directs it to a lock-in amplifier 1234 whose reference is set at 15 KHz from a signal provided by the microprocessor 1208. The lock-in amplifier 1234 further amplifies the signal and directs it to an A-D board 1236 and back into the microprocessor 1208. The lowpass filter 1232 provides the photodetector output except the 2 f signal. This signal provides the microprocessor 1208 with the zero for the system and is also a diagnostic tool.

As was previously indicated, the signal is developed and recorded by the microprocessor 1208 for each cycle of the analyzer. The processor determines the concentration of the component of interest in the gas mixture by computing the absorbance of the gas as a ratio between the zero and the measured value of absorbance at the peak of the absorbance line. The absorbance is a function of the gas pressure and temperature in the cell which are measured by appropriate means 1242 and 1244, respectively, whose outputs are supplied to the A/D board 1236. The absorbance may be adjusted by a pressure/temperature calibration matrix stored in the microprocessor memory 1244. This matrix is developed on an analyzer-by-analyzer basis. Alternatively, one or more corrective calculations may be performed based on measured temperature and pressure in the sample cell or cells.

Once the corrected absorbance value is determined, the concentration of the component of interest in the sample cell may be computed using equation 5, and this may be related to the concentration in the gas mixture using equations 1 and 2. In one implementation, this concentration may be converted into units of, for example lbs/mmscf, averaged four times, and sent to the outputs once per second. Outputs that may be included in this system are a 4-20 mA current loop 1246, a visual display 1250 and RS-232 or comparable serial ports 1252 and 1254. Power for the system is provided by an appropriately chosen power supply 1256. At the end of a sample cycle, the microprocessor 1208 may signal the GC valve controller to purge the sample cell 1216 with carrier gas to prepare for the next sample run.

Although a few variations have been described in detail above, other modifications are possible. For example, the logic flow depicted in the accompanying figures and described herein do not require the particular order shown, or sequential order, to achieve desirable results.

What is claimed is:
1. A method comprising:
    injecting a first sample of a gas mixture containing a component into a first gas chromatography column through which a carrier gas flows, the component being trans- ported by the carrier gas through the first gas chromatography column and eluting from the first gas chromatography column at a known elution time;

supplying the carrier gas and the component eluting from the first gas chromatography column into a sample cell of an absorption spectrometer at the elution time;

passing a light beam through the sample cell;

measuring an absorption of the light beam in the sample cell; and converting the absorption to a concentration of the component in the sample cell.

2. A method as in claim 1, further comprising converting the concentration of the component in the sample cell to a concentration of the component in the gas mixture.

3. A method as in claim 1, further comprising:
operating the first gas chromatography column within a temperature-controlled enclosure; and
executing a programmed temperature ramp program to vary the temperature within the temperature-controlled enclosure after injecting the first sample.

4. A method as in claim 1, further comprising:
simultaneously injecting a second sample of the gas mixture into a second gas chromatography column through which the carrier gas flows, the component being transported by the carrier gas through the second column and eluting from the second column at the known elution time;
supplying the carrier gas and the component from the second column into the sample cell of the absorption spectrometer at the elution time with the carrier gas and the component from the first column.

5. A method as in claim 1, further comprising generating the light beam from a tunable diode laser.

6. A method as in claim 1, further comprising generating the light beam from a laser source selected from a vertical cavity surface emitting laser, a horizontal cavity surface emitting laser, a quantum cascade laser, a distributed feedback laser, and a color center laser.

7. A method as in claim 1, wherein the light beam is generated by a modulated laser source and the absorption spectrum is a harmonic absorption spectrum.

8. A method as in claim 1, wherein the light beam is generated by a modulated laser source and the absorption spectrum is a direct absorption spectrum.

9. A method as in claim 1 wherein the absorption spectrometer is a differential absorption spectrometer.

10. A method as in claim 1, further comprising:
monitoring a temperature within the temperature-controlled enclosure, and automatically injecting the first sample when the temperature is at a predetermined starting temperature.

11. An apparatus comprising:
a first gas chromatography column;
a first injector to deliver a first sample of a gas mixture into the first gas chromatography column;
an absorption spectrometer comprising a sample cell, a laser source that generates a beam of light passing through the sample cell, and a photodetector that quantifies absorption of the light beam in the sample cell;
a gas chromatograph outlet valve to divert gases exiting the gas chromatography column to the sample cell; and
a process controller that controls the injector port to deliver the first sample to the first gas chromatography column at a first time and the gas chromatograph outlet valve to divert the outflow from the first gas chromatography column to the sample cell at a second time that is selected to coincide with a retention time of a component of the first gas mixture.

12. An apparatus as in claim 11, wherein the process controller receives output data from the photodetector, records an absorption spectrum, and calculates a concentration of the component in the gas mixture.

13. An apparatus as in claim 11, wherein the absorption spectrometer further comprises a microprocessor that receives output data from the photodetector, records an absorption spectrum, and calculates a concentration of the component in the gas mixture.

14. An apparatus as in claim 11, further comprising:
a temperature-controlled enclosure comprising an oven heater, the gas chromatography column being positioned within the temperature-controlled enclosure,
and wherein the process controller commands the oven heater to vary the temperature within the temperature-controlled enclosure as a function of time after the first time according to a pre-determined program.

15. An apparatus as in claim 14, further comprising a temperature sensor positioned within the temperature-controlled enclosure, the temperature sensor communicating with the process controller.

16. An apparatus as in claim 15, wherein the process controller monitors an output signal from the temperature sensor and uses the output signal to determine when the temperature-controlled enclosure is at an appropriate temperature to begin an analysis run.

17. An apparatus as in claim 11, wherein the laser source is a tunable diode laser.

18. An apparatus as in claim 11, wherein the laser source is selected from a vertical cavity surface emitting laser, a horizontal cavity surface emitting laser, a quantum cascade laser, a distributed feedback laser, and a color center laser.

19. An apparatus as in claim 11, wherein the laser source is modulated and the absorption spectrum is a harmonic absorption spectrum.

20. An apparatus as in claim 11, wherein the laser source is modulated and the absorption spectrum is a direct absorption spectrum.

21. An apparatus as in claim 11, further comprising:
a scrubber that reduces the concentration of the component; and
one or more scrubber valves that may be operated to direct the gases exiting the first gas chromatography column through the scrubber prior to the sample cell or to bypass the scrubber.

22. An apparatus as in claim 11, further comprising:
one or more second gas chromatography columns; and
one or more second injectors to deliver one or more second samples of a gas mixture into the one or more second gas chromatography columns at the first time.

23. An apparatus comprising:
a first gas chromatography column;
a first injector to deliver a first sample of a gas mixture into the first gas chromatography column;
a gas chromatograph outlet valve to divert gases exiting the gas chromatography column to a sample cell of an absorption spectrometer; and
a process controller that controls the injector port to deliver the first sample to the first gas chromatography column at a first time and the gas chromatograph outlet valve to divert the outflow from the first gas chromatography column at a second time that is selected to coincide with a retention time of a component of the first gas mixture.

24. An apparatus comprising:
means for separating a first component in a gas mixture from one or more other components in the gas mixture;
means for injecting a sample of the gas mixture into the separation means;
means for containing the separated component as it leaves the separation means;
means for producing and directing a beam of light through the contained separated component;
means for recording an absorption spectrum for the separated component; and
processing means for processing the recorded spectrum and calculating a concentration of the component in the gas mixture.

* * * * *